(12) United States Patent
Baril et al.

(10) Patent No.: US 11,596,399 B2
(45) Date of Patent: Mar. 7, 2023

(54) ANVIL BUTTRESS ATTACHMENT FOR SURGICAL STAPLING APPARATUS

(71) Applicant: Covidien LP, Mansfield, MA (US)

(72) Inventors: Jacob C. Baril, Norwalk, CT (US); Roanit Fernandes, Hyderabad (IN)

(73) Assignee: Covidien LP, Mansfield, MA (US)

( * ) Notice: Subject to any disclaimer, the term of this patent is extended or adjusted under 35 U.S.C. 154(b) by 32 days.

(21) Appl. No.: 17/355,244

(22) Filed: Jun. 23, 2021

(65) Prior Publication Data

US 2022/0409201 A1     Dec. 29, 2022

(51) Int. Cl.
*A61B 17/072*     (2006.01)
*A61B 17/068*     (2006.01)

(52) U.S. Cl.
CPC .... *A61B 17/0686* (2013.01); *A61B 17/07292* (2013.01); *A61B 2017/07257* (2013.01); *A61B 2017/07271* (2013.01); *A61B 2017/07285* (2013.01)

(58) Field of Classification Search
CPC .... A61B 17/07292; A61B 2017/07257; A61B 17/072
See application file for complete search history.

(56) References Cited

U.S. PATENT DOCUMENTS

| | | |
|---|---|---|
| 3,054,406 A | 9/1962 | Usher |
| 3,124,136 A | 3/1964 | Usher |
| 3,364,200 A | 1/1968 | Ashton et al. |
| 3,499,591 A | 3/1970 | Green |
| 3,797,494 A | 3/1974 | Zaffaroni |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |

(Continued)

FOREIGN PATENT DOCUMENTS

| | | |
|---|---|---|
| CA | 2282761 A1 | 9/1998 |
| DE | 1602563 U | 3/1950 |

(Continued)

OTHER PUBLICATIONS

Extended European Search Report corresponding to EP 14 16 9739.1, completed Aug. 19, 2014 and Aug. 29, 2014; (7 pp).

(Continued)

*Primary Examiner* — Gloria R Weeks
(74) *Attorney, Agent, or Firm* — Carter, DeLuca & Farrell LLP

(57) ABSTRACT

An anvil buttress loading system includes an anvil assembly, an anvil buttress retention clip coupled to the anvil assembly, an anvil buttress loading tool, and an anvil buttress. The anvil buttress is retainable on each of the anvil buttress loading tool and the anvil assembly, and is transferrable from the anvil buttress loading tool to the anvil assembly.

16 Claims, 13 Drawing Sheets

(56) References Cited

U.S. PATENT DOCUMENTS

| | | |
|---|---|---|
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A * | 11/1998 | Yoon .............. A61B 17/07207 227/176.1 |
| 5,843,096 A | 12/1998 | Igaki et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |

(56) References Cited

U.S. PATENT DOCUMENTS

| | | | |
|---|---|---|---|
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Farinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Farinelli et al. |
| 8,235,273 B2 | 8/2012 | Dlson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 * | 1/2013 | Shah ............... A61B 17/07207 227/19 |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 * | 8/2013 | Marczyk ............... A61B 17/068 623/2.11 |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 * | 12/2013 | Stopek ............... A61B 17/0686 227/176.1 |
| 8,617,132 B2 | 12/2013 | Golzarian et al. |
| 8,631,989 B2 | 1/2014 | Aranyi et al. |
| 8,646,674 B2 | 2/2014 | Schulte et al. |

(56) References Cited

U.S. PATENT DOCUMENTS

| | | |
|---|---|---|
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,272,406 B2 * | 3/2016 | Aronhalt ............ A61B 17/0643 |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | Stopek et al. |
| 9,386,984 B2 * | 7/2016 | Aronhalt ............ A61B 17/072 |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 10,166,023 B2 * | 1/2019 | Vendely ............ A61B 17/07207 |
| 10,349,940 B2 * | 7/2019 | Zeiner ................ A61B 17/068 |
| 11,457,920 B2 * | 10/2022 | Marczyk ............ A61B 17/068 |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0093029 A1 * | 5/2004 | Zubik ................ A61B 17/072 606/219 |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |
| 2006/0025816 A1 * | 2/2006 | Shelton ............ A61B 17/07207 606/215 |
| 2006/0121266 A1 | 6/2006 | Fandel et al. |
| 2006/0173470 A1 | 8/2006 | Dray et al. |
| 2006/0190027 A1 | 8/2006 | Downey |
| 2007/0034669 A1 | 2/2007 | de la Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |

(56) References Cited

U.S. PATENT DOCUMENTS

| | | |
|---|---|---|
| 2009/0031842 A1 | 2/2009 | Kawai et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0087279 A1* | 4/2011 | Shah .............. A61B 17/07207 606/219 |
| 2011/0089220 A1* | 4/2011 | Ingmanson ...... A61B 17/07207 227/176.1 |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2012/0080336 A1 | 4/2012 | Shelton, IV et al. |
| 2012/0116416 A1 | 5/2012 | Neff et al. |
| 2012/0197272 A1 | 8/2012 | Oray et al. |
| 2012/0241491 A1 | 9/2012 | Mdridge et al. |
| 2012/0241493 A1 | 9/2012 | Baxter, III et al. |
| 2012/0253298 A1 | 10/2012 | Henderson et al. |
| 2012/0289979 A1* | 11/2012 | Eskaros .......... A61B 17/07292 606/151 |
| 2013/0153636 A1 | 6/2013 | Shelton, IV et al. |
| 2013/0153641 A1 | 6/2013 | Shelton, IV et al. |
| 2013/0221062 A1* | 8/2013 | Hodgkinson .... A61B 17/07292 227/176.1 |
| 2013/0256380 A1 | 10/2013 | Schmid et al. |
| 2013/0274722 A1* | 10/2013 | Kostrzewski .... A61B 17/00234 606/1 |
| 2014/0048580 A1 | 2/2014 | Merchant et al. |
| 2014/0061280 A1* | 3/2014 | Ingmanson ...... A61B 17/07292 227/176.1 |
| 2014/0131418 A1 | 5/2014 | Kostrzewski |
| 2014/0224686 A1 | 8/2014 | Aronhalt et al. |
| 2014/0239047 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0157321 A1 | 6/2015 | Zergiebel et al. |
| 2015/0196296 A1* | 7/2015 | Swayze .......... A61B 17/07207 227/176.1 |
| 2015/0209045 A1 | 7/2015 | Hodgkinson et al. |
| 2015/0231409 A1 | 8/2015 | Racenet et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1* | 5/2016 | Baxter, III ........... A61B 17/072 227/176.1 |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0310134 A1 | 10/2016 | Contini et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0235612 A1* | 8/2018 | Shelton, IV ...... A61B 17/07292 |
| 2018/0235626 A1* | 8/2018 | Shelton, IV ...... A61B 17/07207 |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | Stopek et al. |
| 2019/0021734 A1 | 1/2019 | Hodgkinson |
| 2019/0059878 A1 | 2/2019 | Racenet et al. |
| 2019/0083087 A1 | 3/2019 | Viola et al. |
| 2020/0015817 A1* | 1/2020 | Harris .............. A61B 17/07207 |
| 2020/0107830 A1* | 4/2020 | Williams ......... A61B 17/07292 |
| 2021/0068827 A1 | 3/2021 | Williams |
| 2021/0106329 A1* | 4/2021 | Williams ............... A61B 17/11 |
| 2021/0177411 A1 | 6/2021 | Williams |
| 2022/0167981 A1* | 6/2022 | Shelton, IV ...... A61B 17/07207 |
| 2022/0313264 A1* | 10/2022 | Shelton, IV ...... A61B 17/07292 |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 2491867 A1 | 8/2012 |
| JP | 2000166933 A | 6/2000 |
| JP | 2002202213 A | 7/2002 |
| JP | 2007124166 A | 5/2007 |
| JP | 2010214132 A | 9/2010 |
| WO | 9005489 A1 | 5/1990 |
| WO | 95/16221 A1 | 6/1995 |
| WO | 98/38923 A1 | 9/1998 |
| WO | 9926826 A2 | 6/1999 |
| WO | 9010456 A1 | 3/2000 |
| WO | 9016684 A1 | 3/2000 |
| WO | 2010075298 A2 | 7/2010 |
| WO | 2022086842 A2 | 4/2022 |

OTHER PUBLICATIONS

Extended European Search Report corresponding to EP 14 15 7997 9, completed Sep. 9, 2014 and dated Sep. 17, 2014; (8 pp).

Extended European Search Report corresponding to EP 14 16 8904 2, completed Sep. 10, 2014 and dated Sep. 18, 2014; (8 pp).

Extended European Search Report corresponding to EP 13 19 4995 0, completed Jun. 5, 2014 and dated Oct. 13, 2014; (10 pp).

Extended European Search Report corresponding to EP 13 15 4571 7, completed Oct. 10, 2014 and dated Oct. 2014; (8 pp).

Extended European Search Report corresponding to EP 14 18 1125 7, completed Oct. 16, 2014 and dated Oct. 24, 2014; (7 pp).

Extended European Search Report corresponding to EP 14 18 1127 3, completed Oct. 16, 2014 and dated Nov. 10, 2014; (8 pp).

Extended European Search Report corresponding to EP 14 19 0419.3, completed Mar. 24, 2015 and dated Mar. 30, 2015; (6 pp).

European Office Action corresponding to EP 12 198 776.2 dated Apr. 7, 2015.

European Office Action corresponding to EP 13 156 297.7 dated Apr. 10, 2015.

Australian Examination Report No. 1 corresponding to AU 2011250822 dated May 18, 2015.

European Office Action corresponding to EP 12 186 175.1 dated Jun. 1, 2015.

Chinese Office Action corresponding to CN 201010517292.8 dated Jun. 2, 2015.

(56) References Cited

OTHER PUBLICATIONS

Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 mailed Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2 016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.

Australian Examination Report No. 1 corresponding to AU 2014227480 dated May 21, 2016.
Australian Examination Report No. 1 corresponding to AU 2012254977 dated May 30, 2016.
European Office Action corresponding to EP 14 17 2681.0 dated May 13, 2016.
Extended European Search Report corresponding to EP 16 15 3647.9 dated Jun. 3, 2016.
Chinese Office Action corresponding to ON 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.

(56) References Cited

OTHER PUBLICATIONS

Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
Australian Examination Report No. 1 corresponding to AU 2014200793 dated Sep. 2, 2017.
Extended European Search Report corresponding to EP 17 17 8528.0 dated Oct. 13, 2 017.
Australian Examination Report No. 1 corresponding to AU 2013234420 dated Oct. 24, 2017.

(56) References Cited

OTHER PUBLICATIONS

Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11,2 017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.
International Search Report and Written Opinion issued in corresponding International Application No. PCT/IB2022/055594 dated Oct. 4, 2022, 13 pages.

\* cited by examiner

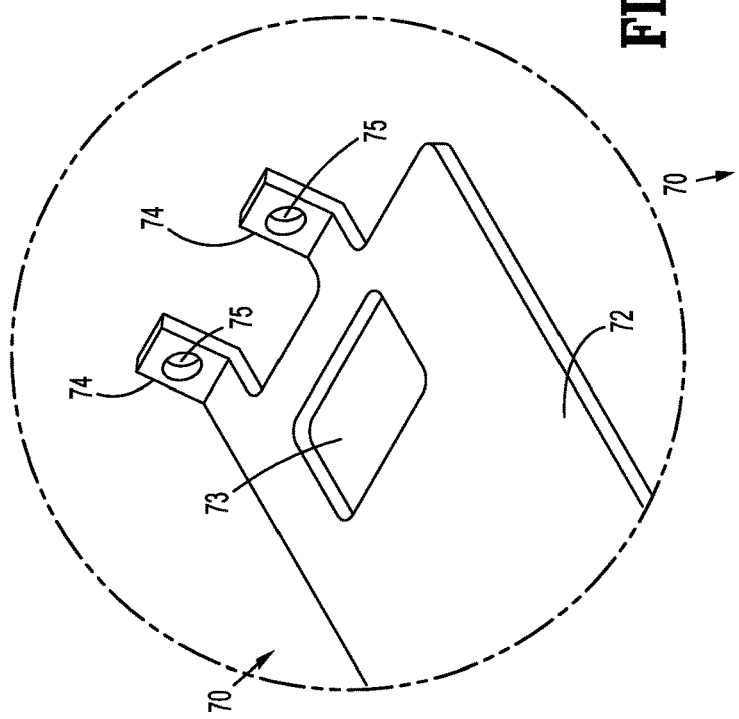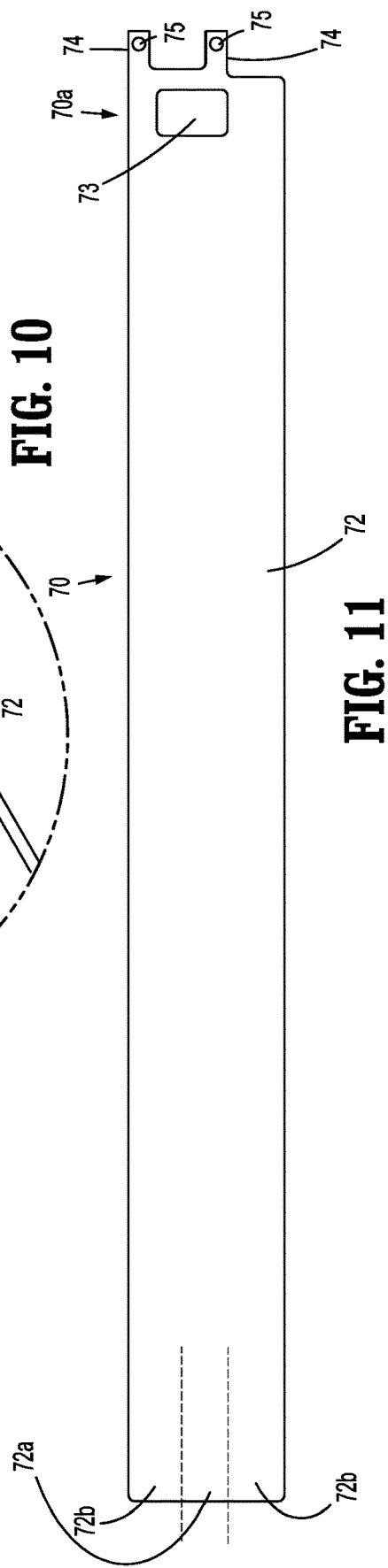
FIG. 10
FIG. 11

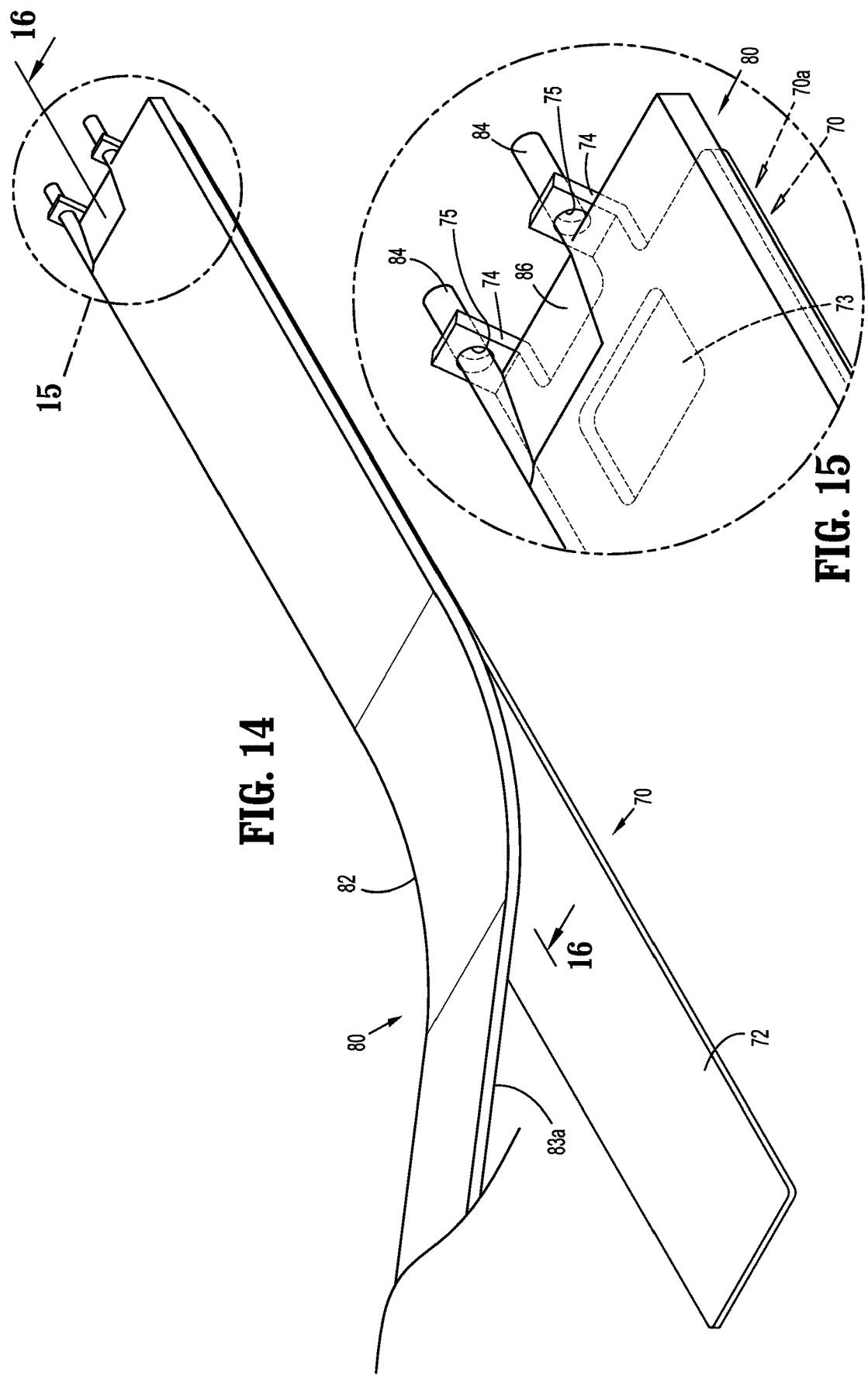

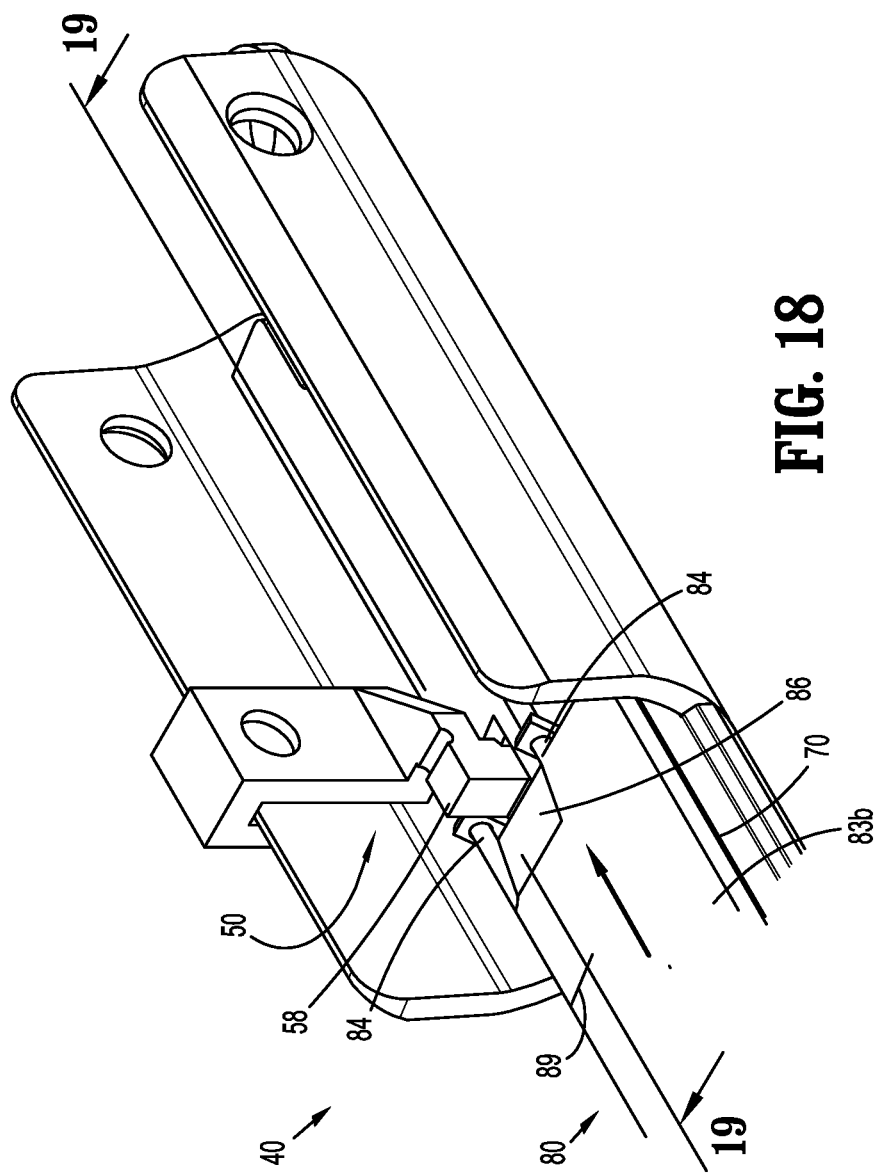

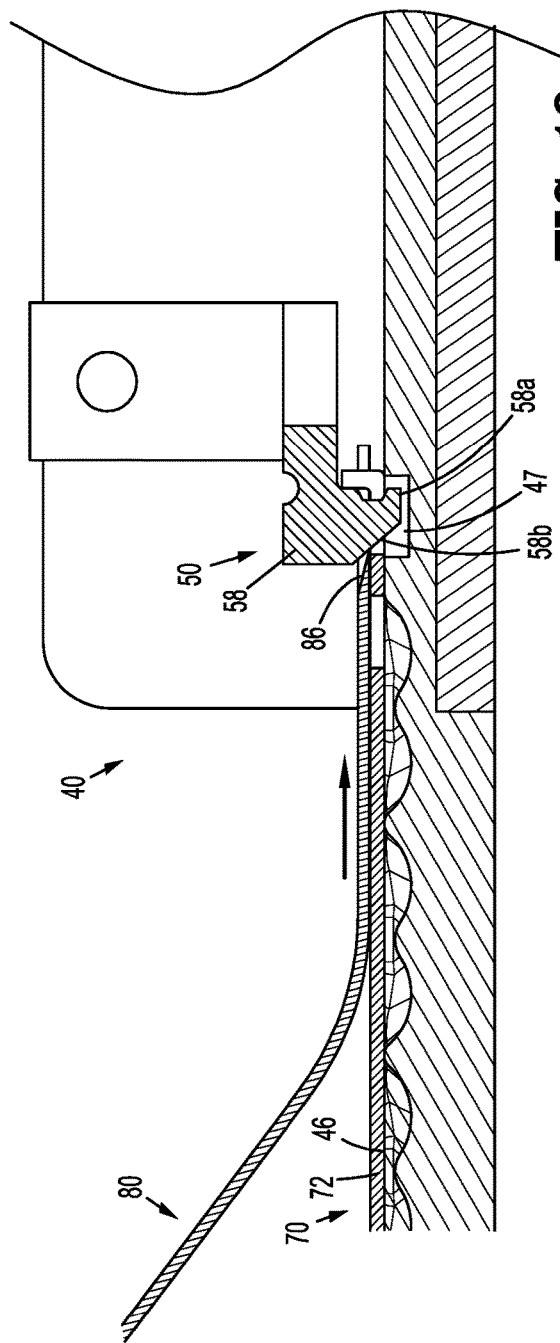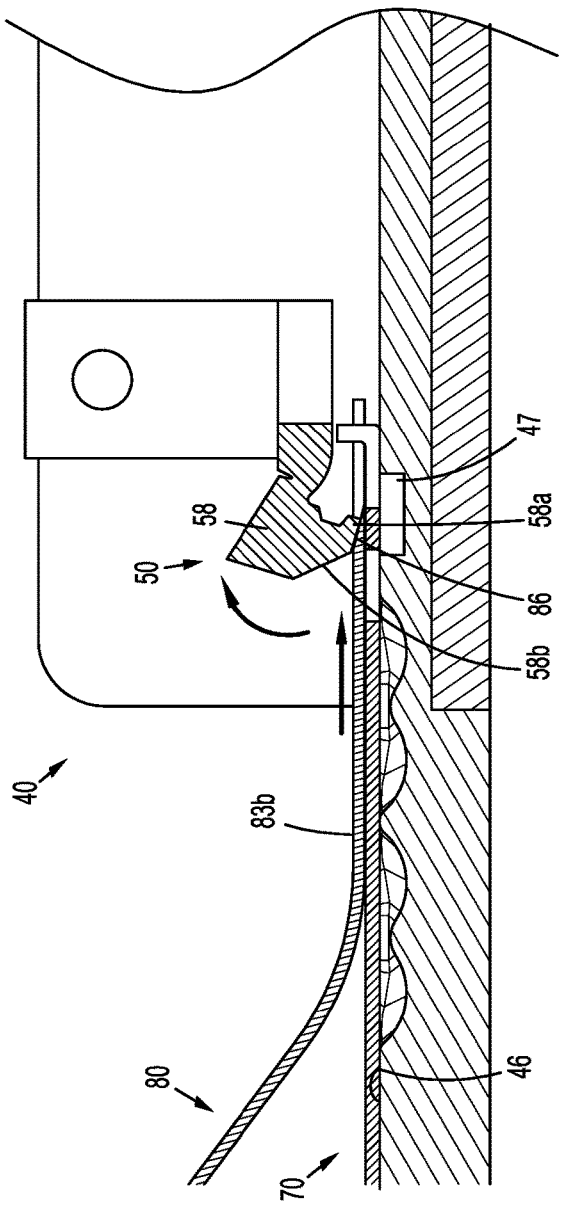

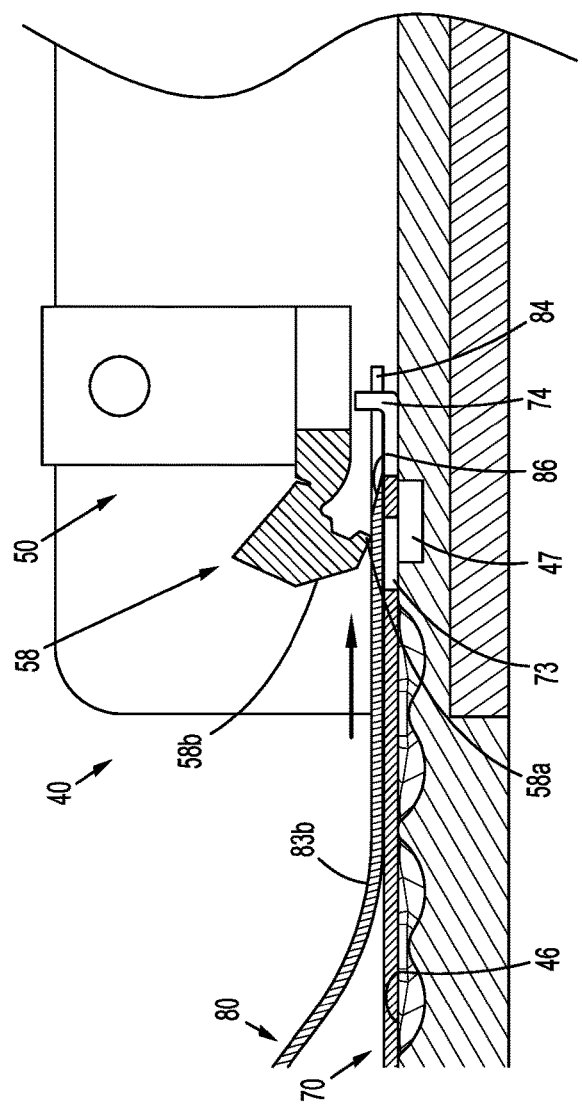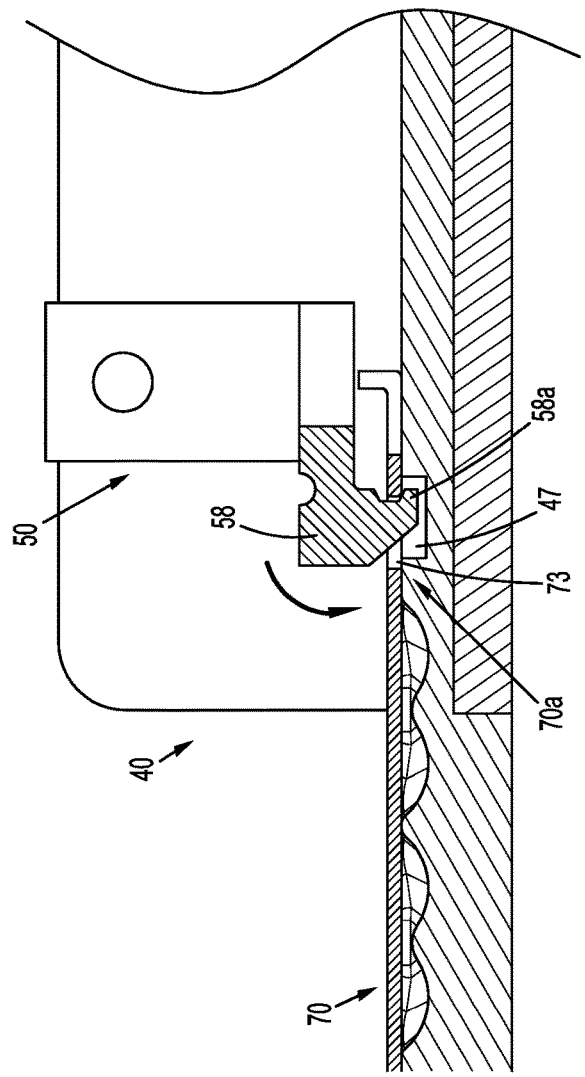

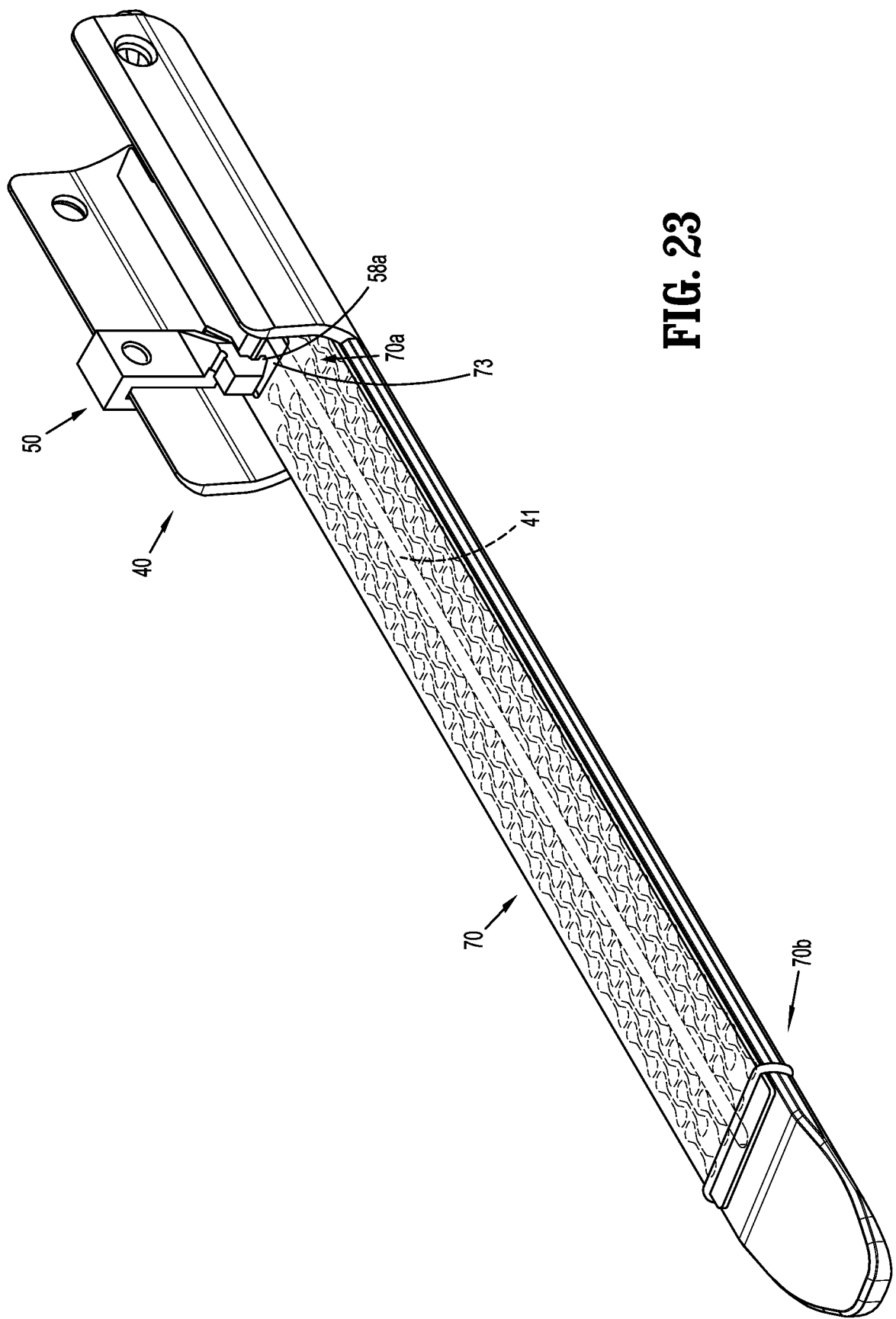

ANVIL BUTTRESS ATTACHMENT FOR SURGICAL STAPLING APPARATUS

FIELD

The present application is generally related to surgical stapling apparatus, and more particularly, to anvil buttress loading systems and assemblies for releasably securing anvil buttresses to the surgical stapling apparatus.

BACKGROUND

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the surgical stapling apparatus is actuated, or "fired", longitudinally moving firing bars contact staple drive members in one of the jaws. The staple drive members push the surgical staples through the body tissue and into an anvil in the opposite jaw which forms the staples. If body tissue is to be removed or separated, a knife blade can be provided in the jaws of the apparatus to cut the body tissue between the lines of staples.

Surgical supports, e.g., meshes or buttress materials, may be used in combination with surgical stapling apparatus to bridge, repair, and/or reinforce tissue defects within a patient. A clinician may manually attach the buttress materials to the surgical stapling apparatus in the operating room during a surgical procedure, or utilize a surgical stapling apparatus including buttress materials pre-installed thereon, e.g., by an expensive automated attachment process. The buttress material reinforces the staple or suture line as well as covers the juncture of the tissues to reduce leakage prior to healing.

SUMMARY

The present disclosure relates to anvil side (single-sided) buttress attachment onto a loading unit of a surgical stapling apparatus. The anvil buttress loading systems and assemblies of the present disclosure are designed to make anvil buttress attachment in the operating room a simple, straight-forward, and cost-effective procedure.

In one aspect, the present disclosure provides an anvil buttress loading system including an anvil assembly, an anvil buttress retention clip, an anvil buttress loading tool, and an anvil buttress. The anvil assembly includes a tissue facing surface defining a plurality of staple forming pockets therein and a cutout disposed proximal of the plurality of staple forming pockets. The anvil buttress retention clip is coupled to the anvil assembly and includes an arm having a hook extending into the cutout of the anvil assembly. The hook is pivotable in and out of the cutout. The anvil buttress loading tool includes a body portion having a pair of posts extending proximally from the body portion. The anvil buttress includes a body having a window defined in a proximal end portion thereof and a pair of tabs extending proximally from the body. The body of the anvil buttress is positionable on the body portion of the anvil buttress loading tool with the pair of tabs engaged with the pair of posts to retain the anvil buttress on the anvil buttress loading unit, and the body of the anvil buttress is positionable on the tissue facing surface of the anvil assembly with the hook extending through the window and into the cutout to retain the anvil buttress on the anvil assembly. The anvil buttress is transferrable from the anvil buttress loading tool to the anvil assembly.

The arm of the anvil buttress retention clip may include a camming surface tapering distally from the hook to a distal end of the arm.

The pair of posts of the anvil buttress loading tool may be laterally spaced and configured to extend on opposed sides of the arm of the anvil buttress retention clip when the anvil buttress loading tool is aligned with the anvil assembly.

The anvil buttress loading tool may include a ramp tapering to a proximal end of the body portion and extending between the pair of posts. The ramp may be configured to move the arm of the anvil buttress retention clip when the anvil buttress loading tool is engaged with the anvil assembly.

The window of the anvil buttress may be sized to extend over the cutout and a central longitudinal slot defined in the anvil assembly when the anvil buttress is positioned on the anvil assembly.

The anvil assembly may include wings disposed on opposed sides of the tissue facing surface. The anvil buttress retention clip may be coupled to one of the wings. The anvil buttress retention clip may include an anvil retaining portion secured to the anvil assembly and a buttress retaining portion including the arm. The anvil retaining portion may include a slot defined therein and the wing may be retained within the slot. The anvil retaining portion may include a peg extending into the slot, and the wing of the anvil assembly may include an opening defined therethrough with the peg extending through the opening. The buttress retaining portion may include a base extending transversely from the anvil retaining portion and the arm may extend distally from the base. The arm may be interconnected to the base about a hinge.

In another aspect, the present disclosure provides a method of loading an anvil buttress onto an anvil assembly including: lifting a hook of an arm of an anvil buttress retention clip out of a cutout defined in a tissue facing surface of the anvil assembly; sliding an anvil buttress onto the tissue facing surface of the anvil assembly until a window defined in a proximal end portion of the anvil buttress is disposed over the cutout; and releasing the hook such that the hook passes through the window of the surgical buttress and back into the cutout of the anvil assembly to secure the proximal end portion of the anvil buttress to the anvil assembly.

The anvil buttress may be releasably secured to an anvil buttress loading tool, and lifting the hook and sliding the surgical buttress may occur simultaneously during sliding the anvil buttress loading tool into contact with the arm. The method may further include: aligning a pair of posts extending proximally from a body portion of the anvil buttress loading tool on opposed sides of the arm of the anvil buttress retention clip, the pair of posts engaged with a pair of tabs of the anvil buttress; and positioning a body of the anvil buttress against the tissue facing surface of the anvil assembly. Aligning the pair of posts and positioning the body of the anvil buttress may occur prior to sliding the anvil buttress loading tool into contact with the arm. Lifting the hook may include contacting the hook with a ramp of the anvil buttress loading tool. Releasing the hook may include sliding the anvil buttress loading tool out of contact with the arm.

The method may further include securing a distal end portion of the surgical buttress to the anvil assembly.

The details of one or more aspects of the disclosure are set forth in the accompanying drawings and the description below. Other aspects, as well as features, objects, and advantages of the aspects described in this disclosure will be apparent from the description and drawings, and from the claims.

BRIEF DESCRIPTION OF DRAWINGS

Various aspects of the present disclosure are described hereinbelow with reference to the drawings, which are incorporated in and constitute a part of this specification, wherein:

FIG. 10 is a close-up view of area of detail 10 in FIG. 3, illustrating a proximal end portion of the anvil buttress;

FIG. 11 is a top view of the anvil buttress of FIG. 3;

FIG. 14 is a perspective view of the anvil buttress loading tool and the anvil buttress of FIG. 3, shown with the anvil buttress loaded onto the anvil buttress loading tool;

FIG. 15 is a close-up view of area of detail 15 in FIG. 14, illustrating the proximal end portions of the anvil buttress loading tool and the anvil buttress;

FIG. 18 is a perspective view of the anvil assembly and the loaded anvil buttress loading tool of FIG. 17, shown with the loaded anvil buttress loading tool positioned on the anvil assembly;

FIG. 19 is a cross-sectional view of the anvil assembly and the loaded anvil buttress loading tool of FIG. 18, taken along section line 19-19 of FIG. 18;

FIGS. 20-22 are cross-sectional views of the anvil assembly and the loaded anvil buttress loading tool of FIG. 19, illustrating installation of the anvil buttress onto the anvil assembly; and FIG. 23 is a bottom, perspective view of the anvil assembly of FIG. 22, shown loaded with the anvil buttress.

DETAILED DESCRIPTION

Figure 1:
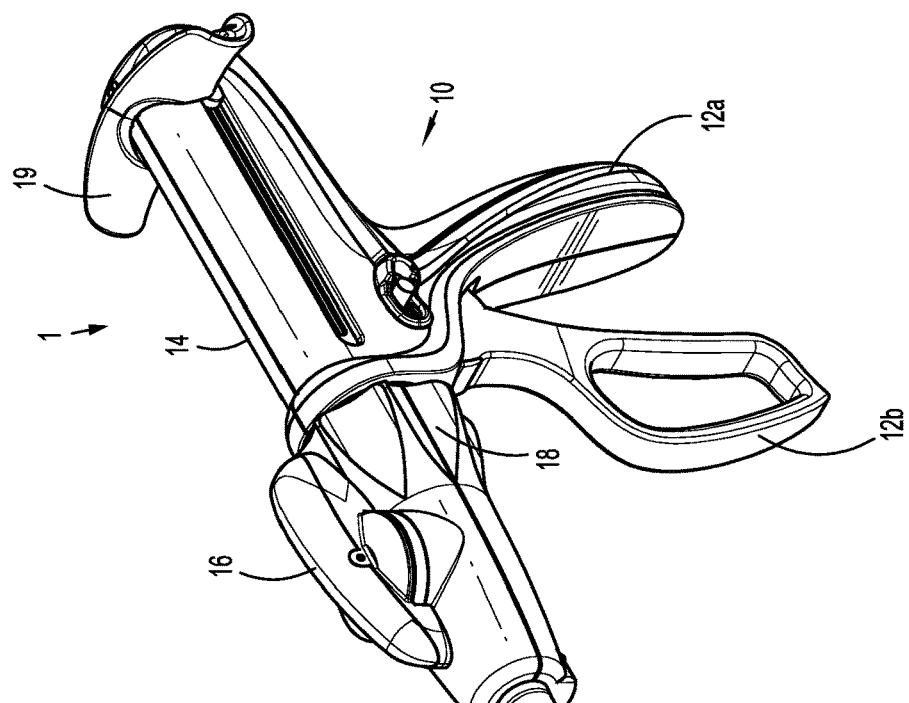
FIG. 1 is a perspective view of a surgical stapling apparatus in accordance with an aspect of the present disclosure.

Aspects of the present disclosure will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user. The terms "generally," "substantially," and "about" shall be understood as words of approximation that take into account relatively little to no variation in the modified terms (e.g., differing by less than 10%). Directional reference terms, such as "downwardly," "upwardly," and the like, are used to ease description of the aspects of this disclosure and are not intended to have any limiting effect on the ultimate orientation of a structure or any part thereof.

Referring now to FIG. 1, an exemplary surgical stapling apparatus or surgical stapler 1 is shown for use in stapling tissue in accordance with aspects of the present disclosure. The surgical stapling apparatus 1 generally includes a handle assembly 10, an elongate tubular body 20 extending distally from the handle assembly 10, and a loading unit 30 extending distally from the elongate tubular body 20. The loading unit 30 includes a housing portion 32 and a tool or jaw assembly 34 including first and second jaw members 34a, 34b. The first jaw member 34a and/or the second jaw members 34b is pivotable with respect to the housing portion 32 such that the tool assembly 34 is movable between an open position in which the first and second jaw members 34a, 34b are spaced apart with respect to each other, and a closed position in which the first and second jaw members 34a, 34b are substantially adjacent each other.

The handle assembly 10 includes a stationary handle member 12a, a movable handle member 12b, and a barrel portion 14. Actuation of the movable handle member 12b applies lines of staples to tissue captured between the first and second jaw members 34a, 34b of the tool assembly 34. An articulation lever 16 is mounted on the forward end of the barrel portion 14 to facilitate articulation of the tool assembly 34. A rotatable member 18 is also mounted on the forward end of the barrel portion 14, adjacent the articulation lever 16. Rotation of the rotatable member 18 relative to the barrel portion 14 rotates the elongate tubular body 20 and the loading unit 30 relative to the handle assembly 10 so as to properly orient the tool assembly 34 relative to tissue to be stapled. A knob 19 is movably positionable along the barrel portion 14. The knob 19 is advanced distally to approximate or close the first and second jaw members 34a, 34b of the tool assembly 34 relative to each other, and retracted proximally to unapproximate or open the first and second jaw members 34a, 34b of the tool assembly 34 with respect to each other.

Figure 2:
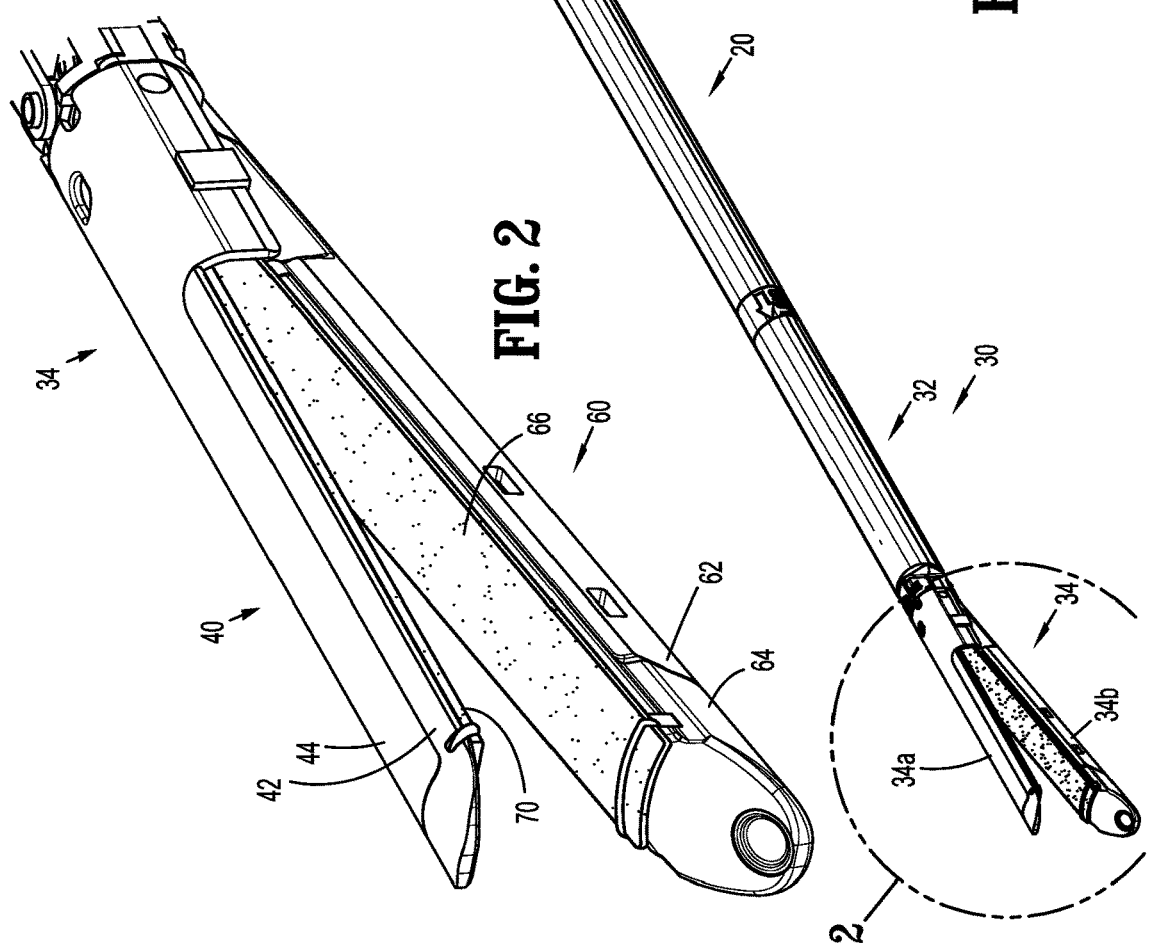
FIG. 2 is a close-up view of area of detail 2 in FIG. 1, illustrating a loading unit of the surgical stapling apparatus.

The loading unit 30 is a disposable loading unit ("DLU") that is releasably secured to the elongated tubular body 20 and thus, replaceable with a new loading unit 30. The loading unit 30 may be a single use loading unit ("SULU") that is used one time and then replaced to facilitate multiples uses of the surgical stapling apparatus 1 on a patient. For example, during a surgical procedure, the surgical stapling apparatus 1 can be used to staple and cut tissue, and the entire SULU is replaced after each staple and cut operation of the surgical stapling apparatus 1. The loading unit 30 may be a multi-use loading unit ("MULU") that is re-useable a predetermined number of times. For example, during a surgical procedure, the surgical stapling apparatus 1 can be used to staple and cut tissue, and a reload assembly (e.g., a staple cartridge 64 as seen in FIG. 2) of the MULU is replaced after each staple and cut operation of the surgical stapling apparatus 1 a pre-determined number of times before the entire MULU needs to be replaced. Alternatively, the loading unit 30 may be permanently affixed to the elongated tubular body 20.

Figure 3:
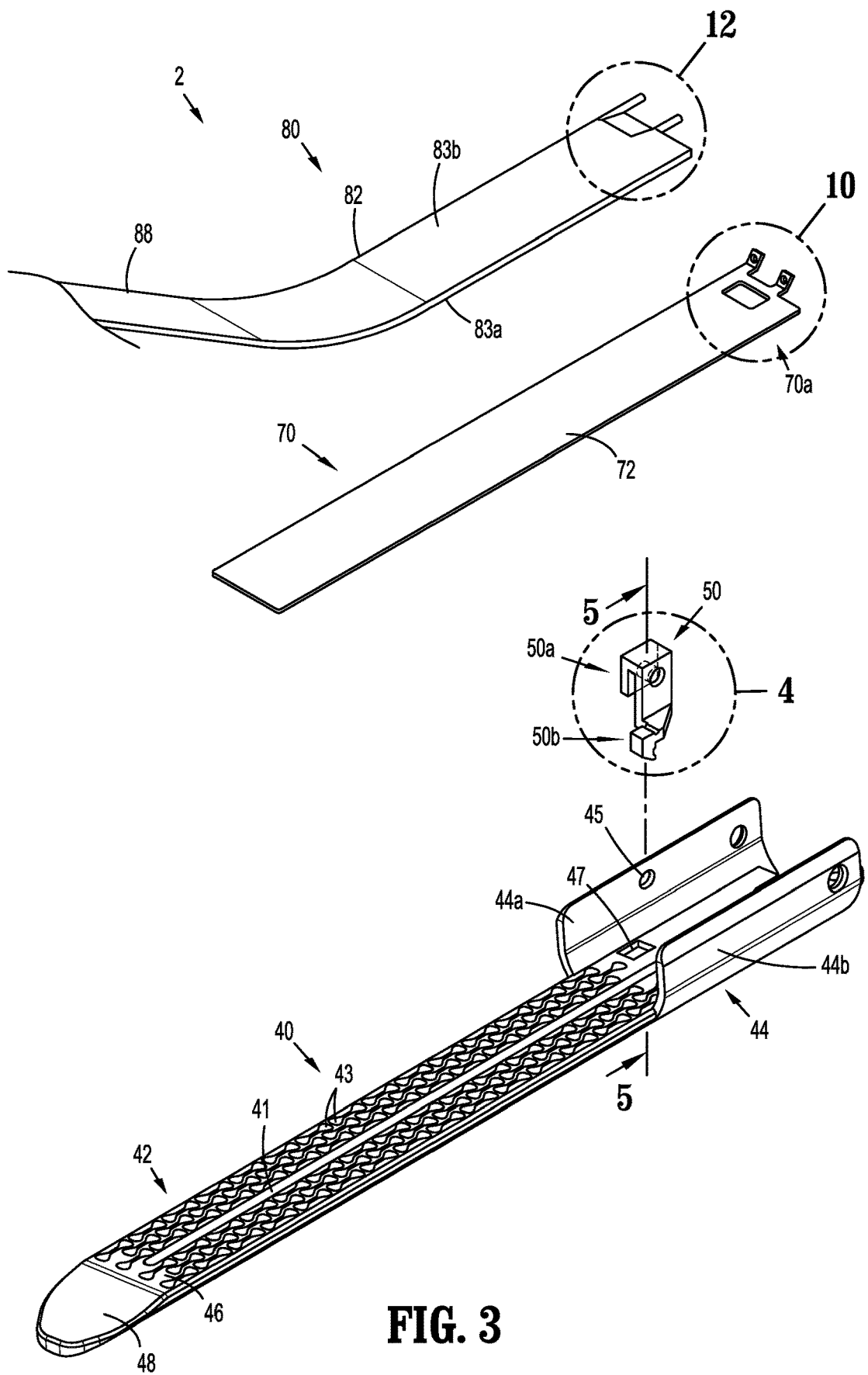
FIG. 3 is a perspective view of an anvil buttress loading system including an anvil assembly of the surgical stapling apparatus of FIG. 1, an anvil buttress retention clip, an anvil buttress, and an anvil buttress loading tool, shown with the components separated.

As shown in FIGS. 1 and 2, the first jaw member 34a of the tool assembly 34 includes an anvil assembly 40 and the second jaw member 34b of the tool assembly 34 includes a staple cartridge assembly 60. The anvil assembly 40 includes an anvil plate 42 and a cover plate 44 secured over the anvil plate 42. While the anvil plate 42 and the cover plate 44 are shown as two separate components, it should be understood that the anvil plate 42 and the cover plate 44 may have a monolithic single-piece construction. As seen in FIG. 3, in conjunction with FIG. 2, the anvil plate 42 has a central longitudinal slot 41 formed therein, a plurality of staple forming pockets or cavities 43 defined in an inward or tissue facing surface thereof 46, and an anvil tip 48 extending distal to the plurality of staple forming pockets 43. The central longitudinal slot 41 is configured for passage of a knife blade (not shown) therethrough during actuation of the surgical stapling apparatus 1. The cover 44 includes a pair of wings 44a, 44b (also referred to herein generally as wings) extending downwardly on opposed sides of the anvil plate 42 proximal to all or a majority of the plurality of staple forming pockets 43 defined in the tissue facing surface 46 of the anvil plate 42. The wings 44a, 44b extend along substantially parallel planes that are substantially orthogonal to a plane defined along the anvil plate 42. An anvil buttress retention clip 50 (also referred to herein generally as a buttress retention clip) is coupled to one of the arms 44a, 44b for releasably securing a proximal end portion of a surgical buttress thereto. The anvil buttress retention clip 50 may be formed from a polymer (e.g., plastic) or metal, and may be releasably or permanently secured to the anvil assembly 40.

With continued reference to FIGS. 1 and 2, the staple cartridge assembly 60 includes a cartridge carrier 62 configured and dimensioned to selectively receive and support a staple cartridge 64 therein. A drive assembly (not shown) is supported in the anvil and staple cartridge assemblies 40, 60 and slidable relative thereto to fire staples (not shown) from the staple cartridge 64 and to cut tissue disposed between the anvil and staple cartridge assemblies 40, 60 during actuation of the surgical stapling apparatus 1.

For a detailed description of the structure and function of exemplary surgical stapling apparatus, including exemplar staple cartridges and drive assemblies, reference may be made to U.S. Pat. Nos. 6,241,139, 6,330,965, and 7,819,896, the entire contents of each of which are incorporated herein by reference. It should be appreciated that principles of the present disclosure are equally applicable to surgical stapling apparatus having other configurations such as, for example, the types described in U.S. Pat. Nos. 5,964,394, 7,128,253, and 7,334,717, the entire contents of each of which are incorporated herein by reference. Accordingly, it should be understood that a variety of surgical stapling apparatus may be utilized with aspects of the present disclosure. For example, laparoscopic or open staplers, such as, for example, GIA™, Endo GIA™, TA™, and Endo TA™ staplers and/or linear and radial reloads with, for example, Tri-Staple™ technology, available through Medtronic (North Haven, Conn.) may be utilized with aspects of the present disclosure.

Turning now to FIG. 3, an anvil buttress loading system 2, including the anvil assembly 40 and the anvil buttress retention clip 50, is shown. The wing 44a of the anvil assembly 40 defines an opening 45 therethrough that is configured to engage an anvil retaining portion 50a of the anvil buttress retention clip 50 therein, and the tissue facing surface 46 of the anvil assembly 40 defines a groove or cutout 47 configured to selectively receive a buttress retaining portion 50b of the anvil buttress retention clip 50 therein. The cutout 47 is disposed proximal to the plurality of staple forming pockets 43 and distal to the opening 45.

Figure 4:
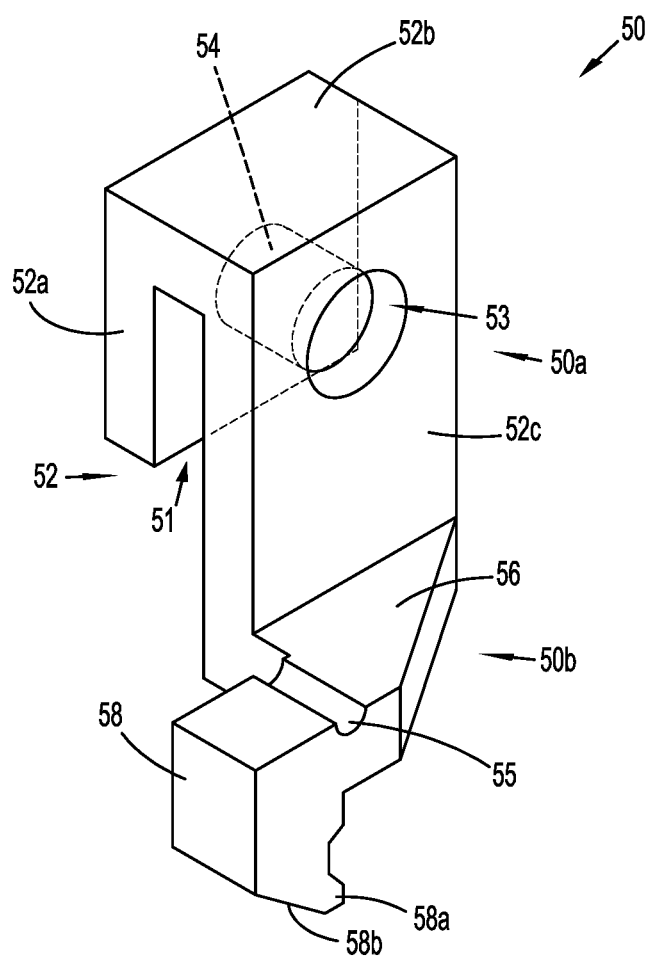
FIG. 4 is a close-up view of area of detail 4 in FIG. 3, illustrating the anvil buttress retention clip.

As shown in FIG. 4, the anvil retaining portion 50a of the anvil buttress retention clip 50 includes a body 52 having first, second, and third walls or portions 52a-c disposed in a substantially u-shaped configuration and defining a slot 51 therein. The first and third walls 52a, 52c are disposed in spaced relation relative to each (e.g., along substantially parallel planes) and are interconnected by the second wall 52b at a first end of the anvil buttress retention clip 50. The slot 51 is sized and shaped to receive the wing 44a (FIG. 3) of the anvil assembly 40 therein. The first wall 52a of the body 52 has a peg or projection 54 (shown in phantom) extending transversely therefrom. The peg 54 extends through the slot 51 and into an aperture 53 defined in the third wall 52c.

The buttress retaining portion 50b includes a base 56 extending transversely from the third wall 52c and an arm 58 extending distally from the base 56. The arm 58 is interconnected to the base 56 about a hinge 55 such that the arm 58 is pivotable relative to the base 56. The arm 58 includes a hook or finger 58a at a terminal end thereof that bends or curves proximally, and a camming surface 58b tapering distally from the hook 58a to a distal end of the arm 58. The arm 58 is biased such that, when the anvil buttress retention clip 50 is coupled to the anvil assembly 40 (FIG. 3), the hook 58a extends into the cutout 47 defined in the tissue facing surface 46 of the anvil plate 42. The arm 58 is pivotable to move the hook 58a out of the cutout 47 upon application of a force against the camming surface 58b.

Figure 7:
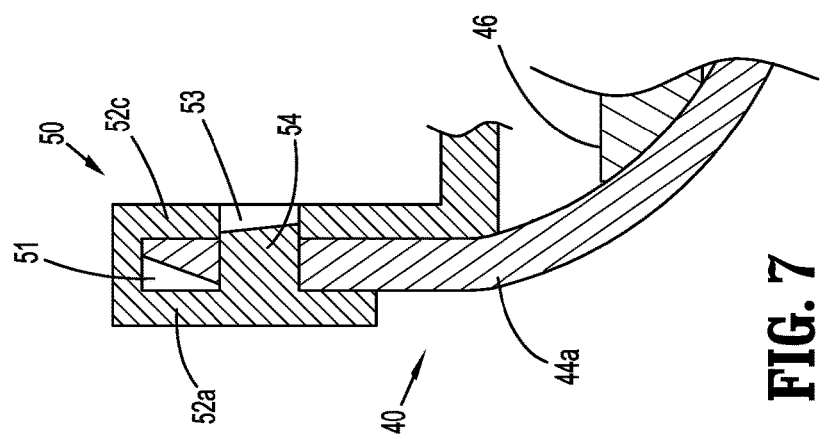
FIGS. 5-7 are cross-sectional views of the anvil buttress retention clip and the anvil assembly of FIG. 3, taken along section line 5-5 of FIG. 3, illustrating installation of the anvil buttress retention clip onto an arm of the anvil assembly.
Figure 6:
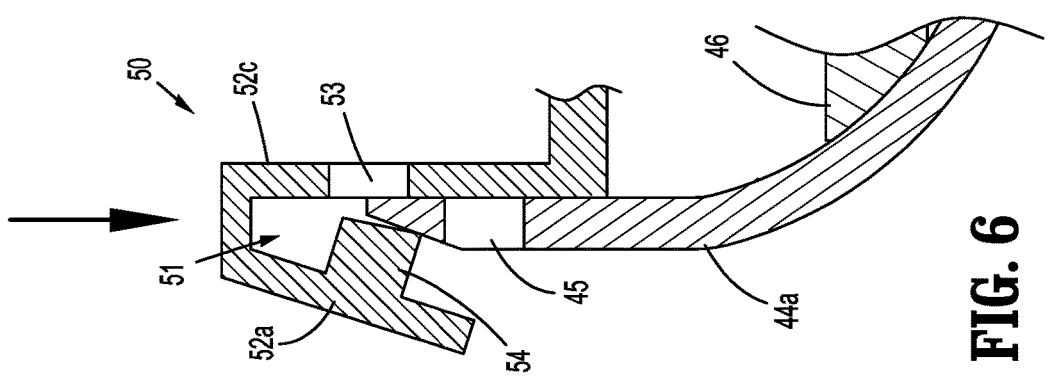
Figure 5:
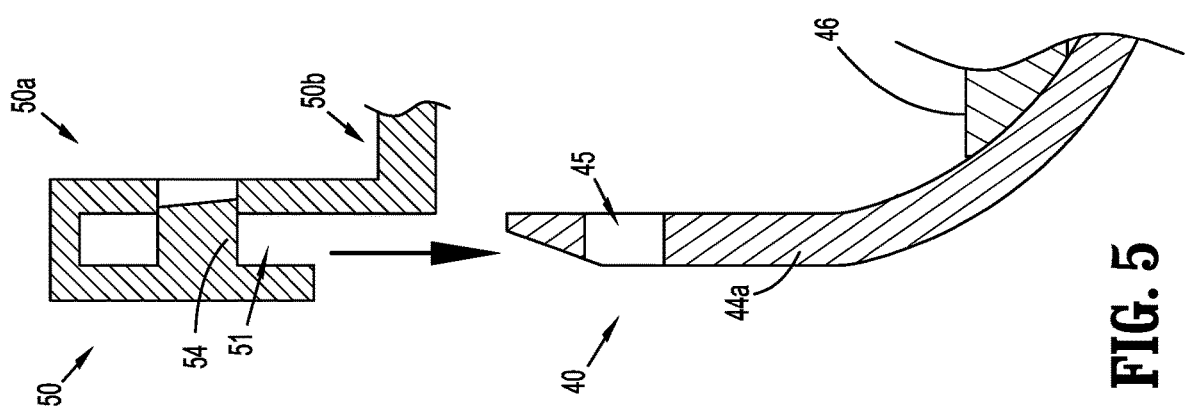
Figure 8:
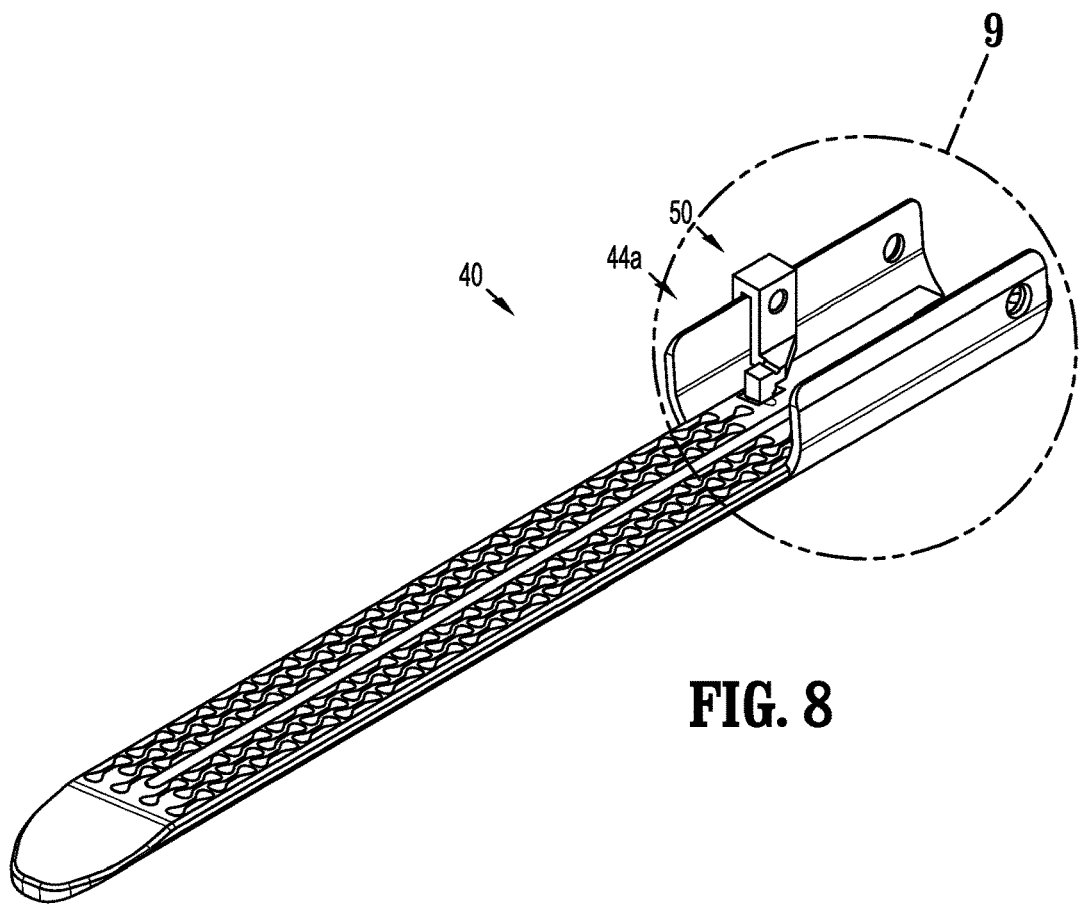
FIG. 8 is a perspective view of the anvil assembly and the anvil buttress retention clip of FIG. 3, shown with the anvil buttress retention clip installed on the anvil assembly.
Figure 9:
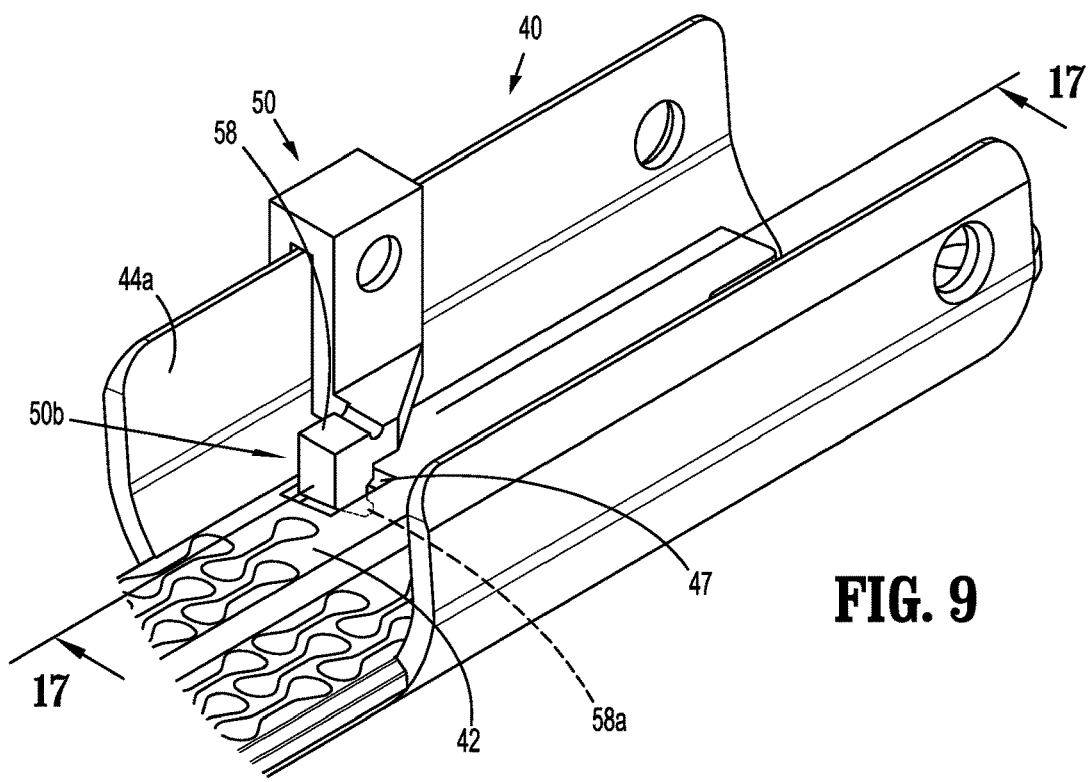
FIG. 9 is a close-up view of area of detail 9 in FIG. 8, illustrating a proximal end portion of the anvil assembly.

As shown in FIGS. 5-7, in a method of securing the anvil buttress retention clip 50 to the wing 44a of the anvil assembly 40, the slot 51 of the anvil retaining portion 50a of the anvil buttress retention clip 50 is aligned with the portion of the wing 44a of the anvil assembly 40 containing the opening 45 and the buttress retaining portion 50b of the anvil buttress retention clip 50 is oriented inside of the wing 44a (e.g., over the tissue facing surface 46 of the anvil assembly 40). The anvil buttress retention clip 50 is then slid onto the wing 44a. During this sliding movement, the peg 54 of the anvil buttress retention clip 50 contacts and slides against the wing 44a, deflecting the first wall 52a of the anvil retaining portion 50a outwardly, as seen in FIG. 6, until the peg 54 catches and enters the opening 45 defined in the wing 44a, as well as the aperture 53 in the third wall 52c of the anvil retention portion 50a, as seen in FIG. 7, securing the anvil buttress retention clip 50 to the anvil assembly 40. As shown in FIGS. 8 and 9, when the anvil buttress retention clip 50 is coupled to the wing 44a of the anvil assembly 40, the arm 58 of the buttress retaining portion 50b is laterally spaced inwardly of the wing 44a with the hook 58a (shown in phantom in FIG. 9) of the arm 58 positioned within the cutout 47 defined in the anvil plate 42. It should be understood that other mating structures and relationships are contemplated to secure the anvil buttress retention clip 50 to the anvil assembly 40 (e.g., interference fit, adhesives, welds, etc.)

With reference again to FIG. 3, the anvil buttress loading system 2 further includes an anvil buttress 70 (also referred to herein generally as a surgical buttress) and an anvil buttress loading tool 80 (also referred to herein generally as a buttress loading tool) for loading the anvil buttress 70 onto the anvil assembly 40. As shown in FIG. 3, as well as FIGS. 10 and 11, the anvil buttress 70 includes a body 72 sized and shaped to cover the tissue facing surface 46 of the anvil assembly 40. The anvil buttress 70 includes a window 73 defined in a proximal end portion 70a thereof. The window 73 extends through a central portion 72a and one of the lateral portions 72b of the body 72 such that, when the anvil buttress 70 is coupled to the anvil assembly 40, the window 73 extends over the central longitudinal slot 41 and the cutout 47 defined in the anvil assembly 40 (FIG. 23). A pair of tabs 74 (also referred to herein generally as tabs) extend proximally from the body 72. The tabs 74 are disposed in spaced relation relative to each other, with one of the tabs 74 extending from the central portion 72a of the body 72 and the other of the tabs 74 extending from the lateral portion 72b of the body 72 containing the window 73. When the anvil buttress 70 is coupled to the anvil assembly 40, the tabs 74 are disposed proximal to, and on opposed sides of the cutout 47 in the anvil assembly 40. Each of the tabs 74 includes an opening 75 extending therethrough that are configured to engage the anvil buttress loading tool 80.

The anvil buttress 70 is fabricated from biocompatible materials which are bioabsorbable or non-absorbable, natural or synthetic materials. It should be understood that a single or combination of natural, synthetic, bioabsorbable, and/or non-bioabsorbable materials may be used to form the anvil buttress 70. In aspects, the anvil buttress 70 is formed from a single sheet of material that is cut to shape. In other aspects, the anvil buttress 70 is formed from a plurality of sheets of material, that are fabricated from the same or different materials, and/or the components (e.g., the body, the tabs, etc.) of the anvil buttress 70 are formed from the same or different materials that are attached to one another by, for example, welding, using adhesive, tying sutures, etc.

The anvil buttress 70 may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The anvil buttress 70 may be a single porous or non-porous layer, or include a plurality of layers including any combination of porous and non-porous layers. For example, the anvil buttress may include multiple porous and non-porous layers that are stacked in an alternating manner. In another example, the anvil buttress may be formed in a "sandwich-like" manner wherein the outer layers are porous and the inner layer(s) are non-porous, or vice versa.

Porous layer(s) in a surgical buttress may enhance the ability of the surgical buttress to absorb fluid, reduce bleeding, and/or seal a wound. Also, the porous layer(s) may allow for tissue ingrowth to fix the surgical buttress in place. Non-porous layer(s) in a surgical buttress may enhance the ability of the surgical buttress to resist tears and perforations during the manufacturing, shipping, handling, and/or stapling processes. Also, non-porous layer(s) may retard or prevent tissue ingrowth from surrounding tissues thereby acting as an adhesion barrier and preventing the formation of unwanted scar tissue.

Figure 12:
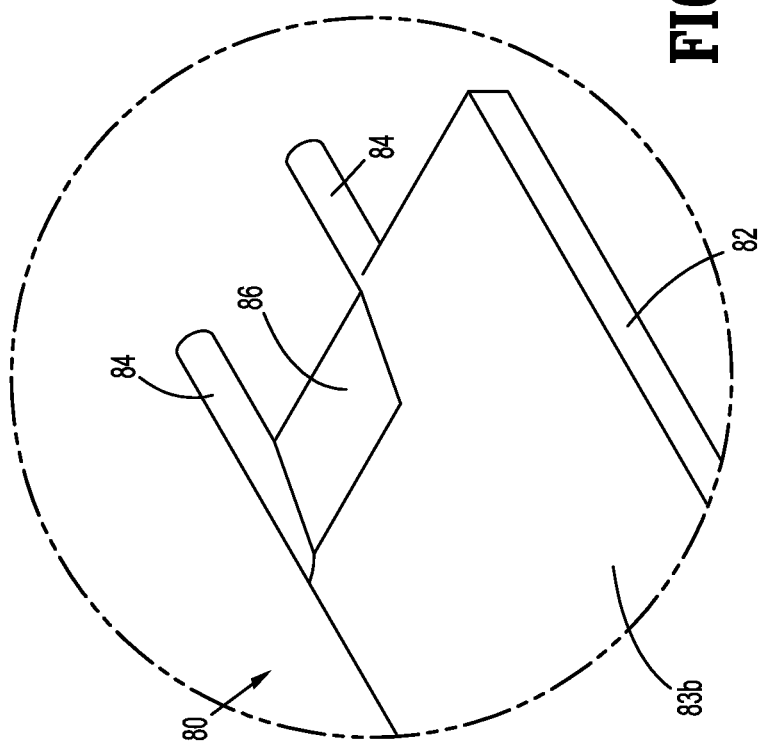
FIG. 12 is a close-up view of area of detail 12 in FIG. 3, illustrating a proximal end portion of the anvil buttress loading tool.
Figure 13:
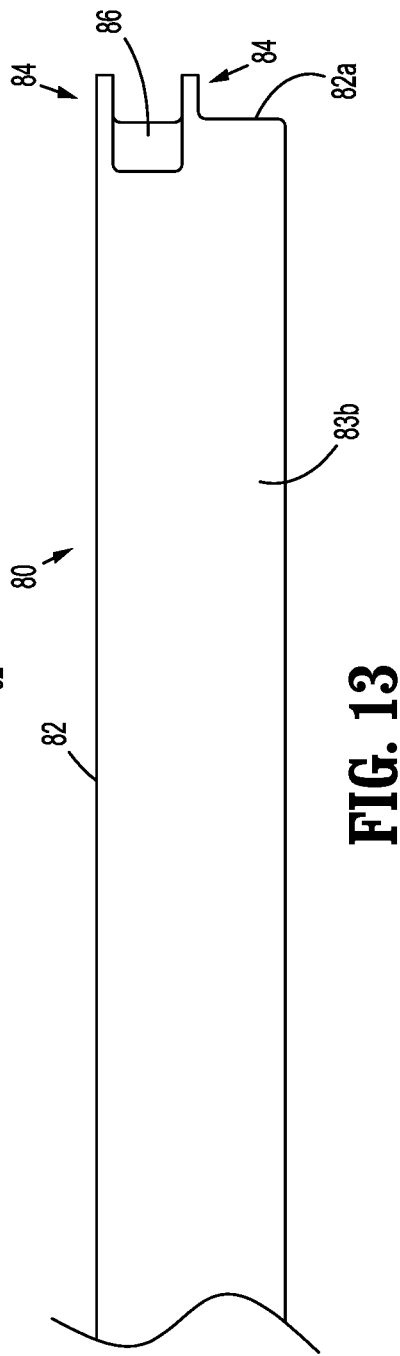
FIG. 13 is a top view of the anvil buttress loading tool of FIG. 3.

With continued reference to FIG. 3, in conjunction with FIGS. 12 and 13, the anvil buttress loading tool 80 is configured to releasably retain the anvil buttress 70 thereon and to engage the anvil assembly 40 for loading the anvil buttress 70 onto the anvil assembly 40 (e.g., transferring the anvil buttress 70 from the anvil buttress loading tool 80 to the anvil assembly 40). The anvil buttress loading tool 80 is formed from a rigid material (e.g., a polymer or metal) and supports the anvil buttress 70 thereon. The anvil buttress loading tool 80 includes a body portion 82 and a pair of posts 84 (also referred to herein generally as posts) extending proximally from a proximal end 82a of the body portion 82. The body portion 82 includes a first or buttress contacting surface 83a for accommodating the body 72 of the anvil buttress 70 thereon and a second or clip contacting surface 83b disposed on an opposed side of the body portion 82 from the first surface 83a. The posts 84 are configured to engage the tabs 74 of the anvil buttress 70. The posts 84 are laterally spaced to align with the tabs 74 of the anvil buttress 70, and are sized and shaped to extend through the openings 75 of the tabs 74. In some aspects, the posts 84 have outer diameters that are smaller than inner diameters of the openings 75 such that the posts 84 are easily slidable into and out of the tabs 74. A ramp 86 is defined in the second surface 83b of the body portion 82. The ramp 86 tapers proximally to the proximal end 82a of the body portion 82. The ramp 86 is sized to extend between the posts 84, and when the anvil buttress loading tool 80 is engaged with the anvil assembly 40, to contact the arm 58 of the anvil buttress retention clip 50. A grip portion 88 may extend distally from the body portion 82 (e.g., be an extension of the body portion 82) for grasping by a user.

Figure 16:
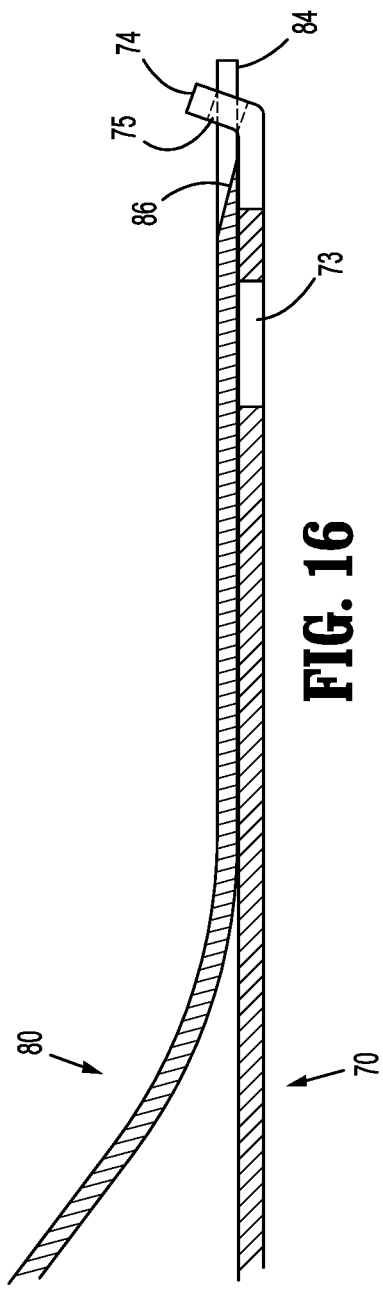
FIG. 16 is a cross-sectional view of the anvil buttress loading tool and the anvil buttress of FIG. 14, taken along section line 16-16 of FIG. 14.

In a method of loading the anvil buttress 70 onto the anvil buttress loading tool 80, as shown in FIGS. 14-16, the body 72 of the anvil buttress 70 is positioned facing the first surface 83a of the body portion 82 of the anvil buttress loading tool 80 and the posts 84 of the anvil buttress loading tool 80 are slid through the openings 75 of the tabs 74 of the anvil buttress 70 to releasably secure the proximal end portion 70a of the anvil buttress 70 to the anvil buttress loading tool 80. Once loaded, the window 73 of the anvil buttress 70 and the ramp 86 of the anvil buttress loading tool 80 are disposed on opposed sides of the anvil buttress loading tool 80. The anvil buttress 70 is engaged with the anvil buttress loading tool 80 only at the tabs 74.

Figure 17:
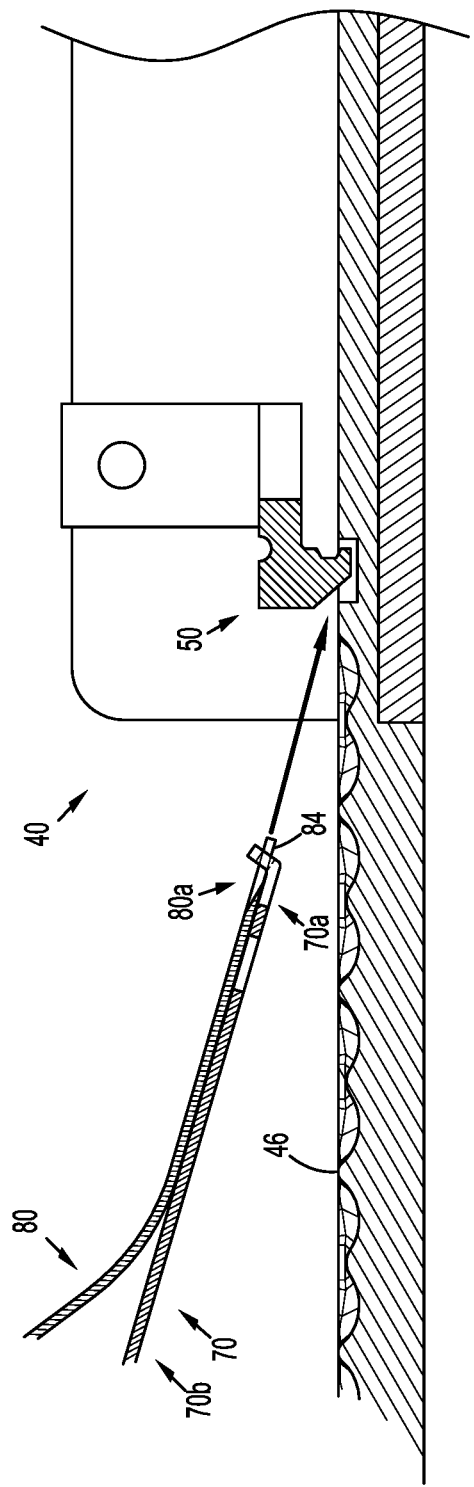
FIG. 17 is a cross-sectional view of the anvil assembly of FIG. 9, taken along section line 17-17 of FIG. 9, and a cross-sectional view of the loaded anvil buttress loading tool of FIG. 16.

Turning now to FIG. 17, the anvil assembly 40 and the anvil buttress loading tool 80 loaded with the anvil buttress 70 are shown in accordance with other aspects of the present disclosure. As shown in FIGS. 17-22, in a method of loading the anvil buttress 70 onto the anvil assembly 40, a proximal end 80a of the anvil buttress loading tool 80, loaded with the anvil buttress 70, is aligned with the anvil assembly 40 such that the anvil buttress 70 faces the tissue facing surface 46 of the anvil assembly 40 and the posts 84 of the anvil buttress loading tool 80 are aligned with the anvil buttress retention clip 50. The proximal end portion 70a of the anvil buttress 70, as described above, is retained on the anvil buttress loading tool 80 by the posts 84 and a distal end portion 70b of the anvil buttress 70 may be held against the body portion 82 of the anvil buttress loading tool 80 by the user during installation. The anvil buttress loading tool 80 is placed adjacent to the anvil assembly 40 with the body 72 of the anvil buttress 70 in contact with the tissue facing surface 46 of the anvil assembly 40 (e.g., the user releases the distal end portion 70b of the anvil buttress 70 onto the tissue facing surface 46) and the posts 84 of the anvil buttress loading tool 80 on opposed sides of the arm 58 of the anvil buttress retention clip 50 such that the ramp 86 is adjacent to the arm 58, as seen in FIGS. 18 and 19.

The anvil buttress loading tool 80 is then slid proximally towards the anvil buttress retention clip 50 such that the ramp 86 contacts the camming surface 58b of the anvil buttress retention clip 50, pivoting and lifting the arm 58 of the anvil buttress retention clip 50 upwardly away from the tissue facing surface 46, and the hook 58a out of the cutout 47 defined in the anvil assembly 40, as seen in FIGS. 20 and 21. During this proximal sliding movement, the arm 58 follows the second surface 83b of the anvil buttress loading tool 80 (e.g., the sloped surface of the ramp 86). The anvil buttress loading tool 80 is slid proximally until the anvil buttress 70 is disposed over (e.g., centered on) the tissue facing surface 46 of the anvil assembly 40. In some aspects, the second surface 83b of the anvil buttress loading tool 80 includes a marking or etching 89 (FIG. 18) thereon that provides an indication to the user of how far the anvil buttress loading tool 80 is to be slid proximally relative to the anvil assembly 40. The marking 89 is disposed on a portion of the second surface 83b of the anvil buttress loading tool 80 that is opposed to the location of the window 73 of the anvil buttress 70 when the anvil buttress 70 is loaded on the anvil buttress loading tool 80 to indicate that the window 73 is positioned over the cutout 47 of the anvil assembly 40.

Once the anvil buttress 70 is positioned over the tissue facing surface 46 of the anvil assembly 40 and the window 73 of the anvil buttress 70 is aligned with the cutout 47, the anvil buttress loading tool 80 is slid distally relative to the anvil assembly 40 to separate the anvil buttress loading tool 80 from the anvil buttress 70. During this distal sliding movement, the posts 84 of the anvil buttress loading tool 80 disengage from the tabs 74 of the anvil buttress 70 as the frictional force between the anvil buttress 70 and the anvil assembly 40 is greater than that of the anvil buttress 70 to the anvil buttress loading tool 80. As the anvil buttress loading tool 80 is removed and clears the anvil buttress retention clip 50, the arm 58 of the anvil buttress retention clip 50 snaps back down so that the hook 58a re-enters the cutout 47 of the anvil assembly 40. As the arm 58 returns to its biased position, the hook 58a passes through the window 73 of the anvil buttress 70, as seen in FIG. 22, thereby capturing the proximal end portion 70a of the anvil buttress 70 to the anvil assembly 40.

As shown in FIG. 23, the proximal end portion 70a of the anvil buttress 70 is retained on the anvil assembly 40 by the passage of the hook 58a of the anvil buttress retention clip 50 through the window 73 of the anvil buttress 70 and the distal end portion 70b of the anvil buttress 70 is retained on the anvil assembly 40 by any suitable attachment feature within the purview of those skilled in the art, such as, for example, mechanical attachment features (e.g., a suture as seen in FIG. 23), chemical attachment features (e.g., adhesive), and/or attachment methods (e.g., welding). The surgical stapling apparatus 1 (FIG. 1), with the anvil assembly 40 loaded with the anvil buttress 70, is ready for use. In aspects, as seen in FIG. 1, the staple cartridge assembly 60 is pre-loaded and/or loaded with a cartridge buttress 66.

In operation, with the loading unit 30 loaded with the anvil buttress 70, as described above, the surgical stapling apparatus 1 is used in accordance with methods known by those skilled in the art. Once the anvil and staple cartridge assemblies 40, 60 are clamped onto tissue, the surgical stapling apparatus 1 is fired, thereby stapling the anvil buttress 70 to the tissue. During firing, a knife (not shown) travels distally through the tool assembly 34 (through the central longitudinal slot 41 of the anvil assembly 40) and substantially simultaneously cuts and divides the tissue and the anvil buttress 70 disposed between the rows of formed staples. As the window 73 of the anvil buttress 70 extends over the central longitudinal slot 41 of the anvil assembly 40, passage of the knife releases the anvil buttress 70 from the anvil buttress retention clip 50 such that, when firing is complete and the anvil and staple cartridge assemblies 40, 60 are unclamped, the anvil buttress 70, which is now stapled to the tissue, pulls away from the anvil assembly 40, and the tool assembly 34 can be removed from the surgical site. The used staple cartridge 64 may then be removed from the tool assembly 34 and replaced with a new staple cartridge 64. A new anvil buttress 70 may be installed onto the anvil assembly 40, as needed or desired, as described above.

While illustrated as being used on a hand-held manually actuated surgical device hereinabove, it is contemplated, and within the scope of the present disclosure for the loading unit 30 to be configured for use with various electromechanical surgical instruments and/or electrosurgical instruments, for example, the loading unit 30 may be configured to be detachably coupleable and controllable by a handheld electromechanical surgical device, such as the handheld electromechanical surgical system shown and described in U.S. Patent Publication No. 2016/0310134, the entire content of which is incorporated herein by reference, or by a robotic surgical system. One exemplary robotic surgical system may generally include a plurality of surgical robotic arms each having an instrument drive unit and the loading unit 30 removably attached thereto; a control device; and an operating console coupled with the control device.

The operating console includes a display device, which is set up in particular to display three-dimensional images; and manual input devices by means of which a person, for example, a surgeon, is able to telemanipulate the robotic arms in a first operating mode, as known in principle to a person skilled in the art. Each of the robotic arms may be composed of a plurality of members, which are connected through joints. The robotic arms may be driven by electric drives that are connected to the control device. The control device (e.g., a computer) is set up to activate the drives, in particular by means of a computer program, in such a way that the robotic arms, the attached instrument drive units, and thus the loading unit 30 execute a desired movement according to a movement defined by means of the manual input devices. The control device may also be set up in such a way that it regulates the movement of the robotic arms and/or of the drives.

The robotic surgical system is configured for use on a patient lying on a surgical table to be treated in a minimally invasive manner by means of the loading unit 30. The robotic surgical system may also include more than two robotic arms, the additional robotic arms likewise being connected to the control device and being telemanipulatable by means of the operating console. The loading unit 30 may also be attached to the additional robotic arm.

The control device may control a plurality of motors, with each motor configured to drive movement of the robotic arms in a plurality of directions. Further, the control device may control the activation of the instrument drive unit to drive various operations of the loading unit 30, and may control a rotation of an internal motor pack of the instrument drive unit to ultimately rotate the loading unit 30 about a longitudinal axis thereof.

The robotic surgical system may further include a surgical instrument holder configured to be coupled with or to the robotic arm. The surgical instrument holder holds the instrument drive unit and the loading unit 30. The surgical instrument holder supports or houses a motor, which receives controls and power from the control device to effect a rotation of an internal motor pack of the instrument drive unit, which results in a rotation of the loading unit 30 about a longitudinal axis thereof. The surgical instrument holder may be slidably mounted onto a rail of the robotic arm and moved along the rail via a motor driven chain or belt or the like to adjust a position of the loading unit 30.

For a detailed description of the construction and operation of a robotic surgical system, reference may be made to U.S. Patent Application Publication No. 2012/0116416, filed on Nov. 3, 2011, entitled "Medical Workstation," the entire contents of which are incorporated by reference herein.

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Additionally, the elements and features shown and described in connection with certain aspects of the disclosure may be combined with the elements and features of certain other aspects without departing from the scope of the present disclosure, and that such modifications and variation are also included within the scope of the present disclosure. Therefore, the above description should not be construed as limiting, but merely as exemplifications of aspects of the disclosure. Thus, the scope of the disclosure should be determined by the appended claims and their legal equivalents, rather than by the examples given.

What is claimed is:

1. An anvil buttress loading system comprising:
    an anvil assembly including a tissue facing surface defining a plurality of staple forming pockets therein and a cutout disposed proximal of the plurality of staple forming pockets;
    an anvil buttress retention clip coupled to the anvil assembly, the anvil buttress retention clip including an arm having a hook extending into the cutout of the anvil assembly, the hook pivotable in and out of the cutout;
    an anvil buttress loading tool including a body portion having a pair of posts extending proximally from the body portion, and a ramp tapering to a proximal end of the body portion and extending between the pair of posts, the ramp configured to move the arm of the anvil buttress retention clip when the anvil buttress loading tool is engaged with the anvil assembly; and
    an anvil buttress including a body having a window defined in a proximal end portion thereof and a pair of tabs extending proximally from the body,
    the body of the anvil buttress positionable on the body portion of the anvil buttress loading tool with the pair of tabs engaged with the pair of posts to retain the anvil buttress on the anvil buttress loading unit, and the body of the anvil buttress positionable on the tissue facing surface of the anvil assembly with the hook extending through the window and into the cutout to retain the anvil buttress on the anvil assembly, the anvil buttress transferrable from the anvil buttress loading tool to the anvil assembly.

2. The anvil buttress loading system according to claim 1, wherein the arm of the anvil buttress retention clip includes a camming surface tapering distally from the hook to a distal end of the arm.

3. The anvil buttress loading system according to claim 1, wherein the pair of posts of the anvil buttress loading tool are laterally spaced and configured to extend on opposed sides of the arm of the anvil buttress retention clip when the anvil buttress loading tool is aligned with the anvil assembly.

4. The anvil buttress loading system according to claim 1, wherein the window of the anvil buttress is sized to extend over the cutout and a central longitudinal slot defined in the anvil assembly when the anvil buttress is positioned on the anvil assembly.

5. The anvil buttress loading system according to claim 1, wherein the anvil assembly includes wings disposed on opposed sides of the tissue facing surface, and the anvil buttress retention clip is coupled to one of the wings.

6. The anvil buttress loading system according to claim 5, wherein the anvil buttress retention clip includes an anvil retaining portion secured to the anvil assembly and a buttress retaining portion including the arm.

7. The anvil buttress loading system according to claim 6, wherein the anvil retaining portion includes a slot defined therein and the wing is retained within the slot.

8. The anvil buttress loading system according to claim 7, wherein the anvil retaining portion includes a peg extending into the slot, and the wing of the anvil assembly includes an opening defined therethrough, the peg extending through the opening.

9. The anvil buttress loading system according to claim 6, wherein the buttress retaining portion includes a base extending transversely from the anvil retaining portion and the arm extends distally from the base.

10. The anvil buttress loading system according to claim 9, wherein the arm is interconnected to the base about a hinge.

11. A method of loading an anvil buttress onto an anvil assembly, comprising:
    lifting a hook of an arm of an anvil buttress retention clip out of a cutout defined in a tissue facing surface of the anvil assembly;
    sliding an anvil buttress onto the tissue facing surface of the anvil assembly until a window defined in a proximal end portion of the anvil buttress is disposed over the cutout; and
    releasing the hook such that the hook passes through the window of the surgical buttress and back into the cutout of the anvil assembly to secure the proximal end portion of the anvil buttress to the anvil assembly.

12. The method according to claim 11, wherein the anvil buttress is releasably secured to an anvil buttress loading tool and, wherein lifting the hook and sliding the surgical buttress occur simultaneously during sliding the anvil buttress loading tool into contact with the arm.

13. The method according to claim 12, further comprising:
    aligning a pair of posts extending proximally from a body portion of the anvil buttress loading tool on opposed sides of the arm of the anvil buttress retention clip, the pair of posts engaged with a pair of tabs of the anvil buttress; and
    positioning a body of the anvil buttress against the tissue facing surface of the anvil assembly,
    wherein aligning the pair of posts and positioning the body of the anvil buttress occur prior to sliding the anvil buttress loading tool into contact with the arm.

14. The method according to claim 12, wherein lifting the hook includes contacting the hook with a ramp of the anvil buttress loading tool.

15. The method according to claim 12, wherein releasing the hook includes sliding the anvil buttress loading tool out of contact with the arm.

16. The method according to claim 11, further comprising securing a distal end portion of the surgical buttress to the anvil assembly.

\* \* \* \* \*